(12) United States Patent
Kim

(10) Patent No.: US 9,404,879 B2
(45) Date of Patent: Aug. 2, 2016

(54) APPARATUS FOR MEASURING ELECTRICAL CONDUCTIVITY IN LIQUID

(71) Applicant: Nam Tae Kim, Yeonje-gu Busan (KR)

(72) Inventor: Nam Tae Kim, Yeonje-gu Busan (KR)

( * ) Notice: Subject to any disclaimer, the term of this patent is extended or adjusted under 35 U.S.C. 154(b) by 0 days.

(21) Appl. No.: 14/008,744

(22) PCT Filed: May 20, 2013

(86) PCT No.: PCT/KR2013/004383
§ 371 (c)(1),
(2) Date: Sep. 30, 2013

(87) PCT Pub. No.: WO2013/183870
PCT Pub. Date: Dec. 12, 2013

(65) Prior Publication Data
US 2015/0097588 A1    Apr. 9, 2015

(30) Foreign Application Priority Data

Jun. 5, 2012    (KR) .................. 10-2012-0060140

(51) Int. Cl.
| | | |
|---|---|---|
| *G01R 27/08* | (2006.01) | |
| *G01N 27/08* | (2006.01) | |
| *G01N 27/04* | (2006.01) | |
| *G01N 27/20* | (2006.01) | |
| *C12Q 1/00* | (2006.01) | |
| *B01L 1/00* | (2006.01) | |
| *G01R 27/22* | (2006.01) | |

(52) U.S. Cl.
CPC .............. *G01N 27/08* (2013.01); *G01N 27/046* (2013.01); *G01N 27/20* (2013.01); *B01L 1/00* (2013.01); *B01L 2200/00* (2013.01); *C12Q 1/00* (2013.01); *G01R 27/22* (2013.01)

(58) Field of Classification Search
CPC ......... B01L 1/00; B01L 2200/00; C12Q 1/00; C12Q 2304/00; G01N 1/00; G01N 2201/00
See application file for complete search history.

(56) References Cited

U.S. PATENT DOCUMENTS

| | | | |
|---|---|---|---|
| 5,959,455 A * | 9/1999 | Brown ................ | G01N 27/023 324/445 |
| 2005/0129575 A1* | 6/2005 | Partridge et al. ................ | 422/62 |
| 2005/0194250 A1* | 9/2005 | Frey ..................... | C12Q 1/6837 204/403.01 |
| 2009/0210169 A1* | 8/2009 | Potyrailo et al. ................ | 702/25 |
| 2009/0278528 A1* | 11/2009 | Partsch ................ | G01N 27/023 324/204 |
| 2011/0163756 A1* | 7/2011 | Wang .................... | G01N 27/023 324/537 |
| 2011/0312841 A1* | 12/2011 | Silverbrook et al. ........... | 506/40 |

* cited by examiner

*Primary Examiner* — Huy Q Phan
*Assistant Examiner* — Temilade Rhodes-Vivour
(74) *Attorney, Agent, or Firm* — Porzio, Bromber & Newman, PC

(57) ABSTRACT

An apparatus for measuring electrical conductivity of liquid is disclosed. The present invention as disclosed accurately and consistently measures infinitesimal conductivity of liquid by applying a stable reference signal to a conductivity sensor controlled with a constant temperature, and by low-noise processing on an output signal from the conductivity sensor. More specifically, infinitesimal conductivity of liquid can be repeatedly and accurately measured and change in performance of the detection apparatus over time can be minimized, by minimizing temperature variations, unstability of a reference signal, and noise effects to ensure stablility of a baseline as a measurement reference of the conductivity and accuracy of conductivity measurements.

32 Claims, 3 Drawing Sheets

APPARATUS FOR MEASURING ELECTRICAL CONDUCTIVITY IN LIQUID

TECHNICAL FIELD

The present invention relates to an apparatus for measuring infinitesimal electrical conductivity of liquid, and more particularly, to an apparatus for measuring electrical conductivity of liquid which accurately and consistently measures electrical conductivity of liquid by applying a stable reference signal to a conductivity sensor controlled with a constant temperature, and by low-noise processing on an output signal from the conductivity sensor.

BACKGROUND ART

Liquid conductivity detectors in the related art have been used to measure a contamination level of drinking water, purity of water for a boiler, a contamination level of lubricant in heavy machinery, performance of a battery electrolyte, a concentration of a chemical material in a fluid analysis system, and the like.

Since liquid conductivity in the applications, in general, has relatively high values, the conductivity detectors is configured of a conductivity sensor configured to operate at room temperature and a detection circuit constructed using an open loop signal generator and a asynchronous demodulator easily fabricated.

A sensor and an apparatus for measuring electric conductivity are disclosed in Korean Patent No. 10-741042 (2007 Jul. 12).

In the sensor for measuring electrical conductivity which measures electrical conductivity in water, a sensor and an apparatus for measuring electric conductivity in the related art as illustrated in FIG. 1 includes a voltage generating circuit 400 for generating an electrical signal having a predetermined frequency and amplitude, an output electrode 302 for outputting the electrical signal supplied from the voltage generating circuit 400; one or more compensation electrodes 304 and 306 for receiving the electrical signal from the output electrode 302; a compensation-electrode compensating circuit 404 for compensating the electrical signal applied from the voltage generating circuit 400 to the output electrode 302; an input electrode 308 for receiving the electrical signal from the output electrode 302; a current measuring circuit 406 for detecting the electrical signal received in the input electrode 308; and a signal amplification and processing circuit 408 for amplifying and processing the current signal and transmitting the processed signal to an external apparatus in a remote place.

The detector in the related art has problems in that considerable fluctuations of a baseline as a reference for the measurements and measured conductivity, due to noise effects by asynchronous detection, unstability of a reference signal, and difficulty in constantly mataining the temperature of a conductivity sensor. Therefore, theses variations become factors that limit a dynamic range in conductivity measurement of liquid including an infinitesimal amount of ions. Further, due to these problems, the conductivity detector in the related art is difficult to be used in conductivity measurement of liquid having an infinitesimal ion concentration.

DETAILED DESCRIPTION OF THE INVENTION

Technical Problem

The present invention has been made to overcome the problems, and its objective is to provide a conductivity detector capable of accurately and consistently measuring infinitesimal conductivity of liquid, and minizing fluctuations in the performance of the detection apparatus over time, by minimizing temperature variations, unstability of a reference signal, and noise effects to ensure the stability of baseline as a measurement reference of the conductivity and accuracy of conductivity measurements.

Solution to Problem

To achieve the objective, the present invention provides an apparatus for measuring electrical conductivity of liquid, including a conductivity sensor configured to detect conductivity of liquid and convert the conductivity into a current; a temperature control unit configured to collect a temperature of the conductivity sensor and control a heater in the conductivity sensor; a reference signal generator configured to generate a reference signal and supply the signal to the conductivity sensor; a current-to-voltage converting unit configured to convert the current output from the conductivity sensor into a low-noise voltage; a lock-in detector configured to synchronously demodulate and filter an output voltage signal from the current-to-voltage converting unit, and amplify the signal to a desired level; and a signal-processing and control unit configured to not only receive the temperature collected in temperature control unit and generate control commands to constantly maintain the temperature of the conductivity sensor at a level set to be higher than room temperature of a measurement environment by setting of measurement conditions, but also calculate the liquid conductivity using a voltage signal from the lock-in detector, provide signal processing, and generate various control commands according to the setting of measurement conditions.

The conductivity sensor may include an inlet tube and an outlet tube configured to guide the liquid; and a flow cell with a constant cross section and a fixed length that is connected to the inlet tube at a cross section and the outlet tube at the other cross section, also includes a reference-signal supply terminal formed in one side thereof to supply a reference signal to the flow cell and a conductivity detection terminal formed in the other side thereof to detect a current signal generated in proportional to the conductivity of the liquid flowing therein.

The conductivity sensor may include a heater configured to heat the liquid flowing in the flow cell.

The conductivity sensor may include a temperature sensor configured to detect a temperature of the liquid.

The reference-signal supply terminal may be formed in a plural number at least two locations of the flow cell.

The conductivity detection terminal may be formed in a plural number at least two locations of the flow cell.

The inlet and outlet tubes may be formed of fluororesin.

The temperature control unit may include a temperature-signal processing circuit configured to process an output signal from a temperature sensor and transmit the signal to the signal-processing and control unit so as to keep the temperature of the flow cell at a desired constant level.

The temperature control unit may include a heater control circuit configured to receive temperature control commands from the signal-processing and control unit and control the heater in the conductivity sensor.

The reference signal generator may include an oscillator configured to generate a stable reference signal with a specific amplitude and frequency.

The reference signal generator may include an automatic gain control (AGC) circuit configured to control the amplitude of the reference signal generated by the oscillator to be constant.

The current-to-voltage converting unit may include a current-to-voltage converter configured to convert a current output from the conductivity sensor into a low-noise voltage.

The current-to-voltage converting unit may include an offset adjustment circuit configured to adjust an output offset value of the current-to-voltage converter.

The current-to-voltage converting unit may include a switch circuit configured to set a measurement range of the conductivity.

The current-to-voltage converting unit may include a switch control circuit configured to control the switch circuit.

The lock-in detector may include a synchronous demodulator configured to synchronously detect the signal output from the current-to-voltage converting unit.

The lock-in detector may include a secondary filter and amplifier configured to filter and amplify a signal output from the synchronous demodulator.

The lock-in detector may include a primary filter and amplifier configured to filter and amplify the output signal from the current-to-voltage converting unit and to transmit the filtered and amplified signal to the synchronous demodulator.

The lock-in detector may include a phase shifter configured to adjust the phase of a reference signal and synchronize the reference signal with the input signal of the synchronous demodulator.

The signal-processing and control unit may include a microcomputer configured to process conductivity and temperature signals, and generate temperature control commands.

The signal-processing and control unit may include an analog and digital communication circuit configured to transmit a conductivity signal received from the lock-in detector or a flow cell temperature received from the temperature control unit to an external apparatus.

The signal-processing and control unit may include a measurement-condition setting unit configured to set conductivity measurement conditions of the apparatus for measuring electrical conductivity of liquid.

The signal-processing and control unit may include a measurement-condition and measurement-state display unit configured to display the conductivity measurement conditions set by the measurement-condition setting unit and measurement states on a display device.

The microcomputer may generate control commands to the switch control circuit so as to adjust the conductivity measurement range.

The apparatus may further include one or more noise-shielding transmission lines configured to connect any one component among the reference signal generator, the current-voltage converting unit, and the temperature control unit to the conductivity sensor, or connect the lock-in detector to the reference signal generator.

Advantageous Effects of Invention

The apparatus for measuring electrical conductivity of liquid having the above-described configuration according to the present invention is effective in consistantly and accurately measuring infinitesimal conductivity of liquid, and minizing change in the performance of the detection apparatus over time, by minimizing temperature variations, unstability of a reference signal, and noise effects to ensure the stability of baseline as a measurement reference of the conductivity and accuracy of conductivity measurements.

BEST MODES FOR CARRYING OUT THE INVENTION

Hereinafter, a preferred embodiment of the present invention will be described in detail with reference to the accompanying drawings.

Figure 1:
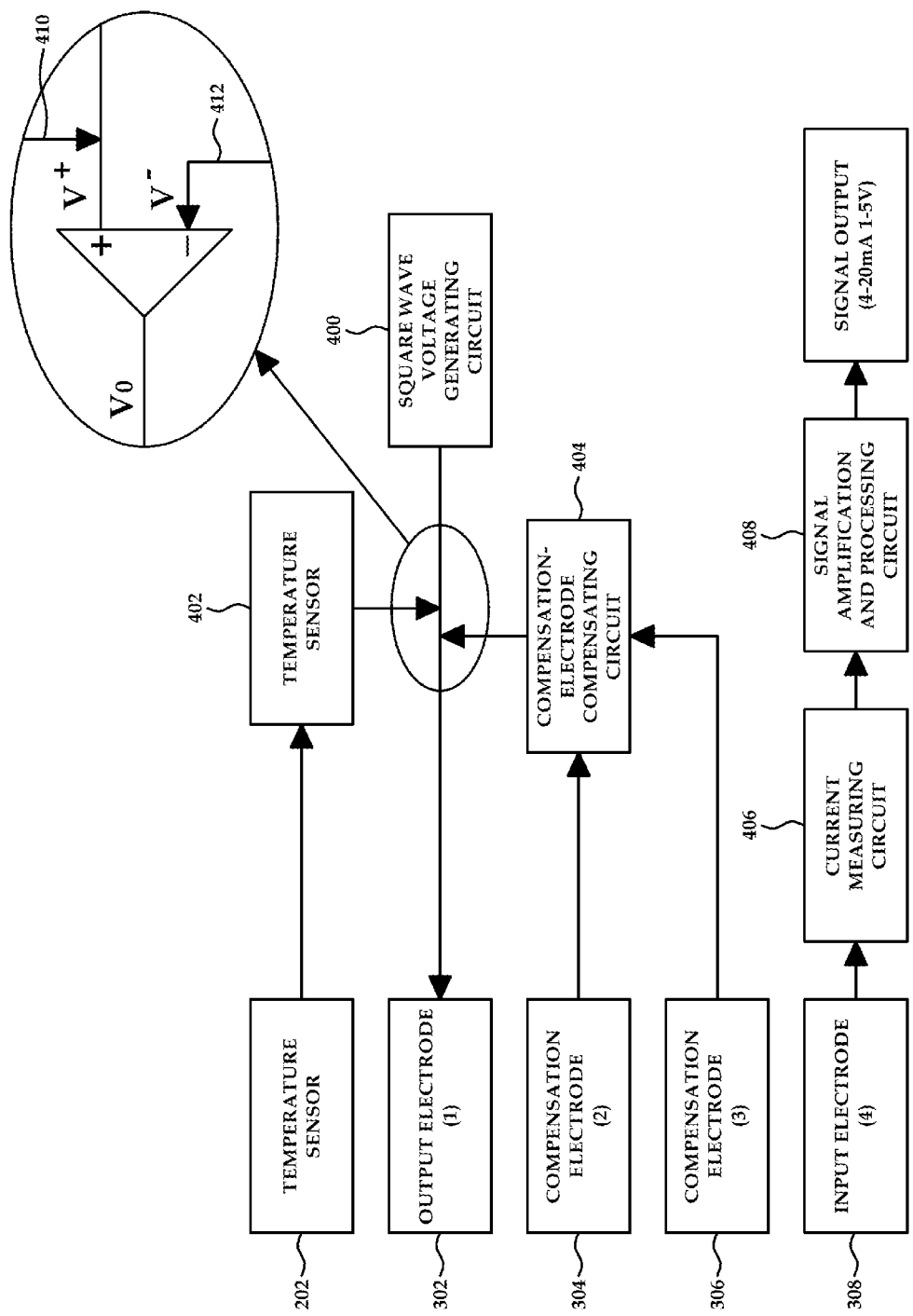
FIG. 1 is a block diagram illustrating a sensor and an apparatus for measuring electrical conductivity in the related art.
Figure 2:
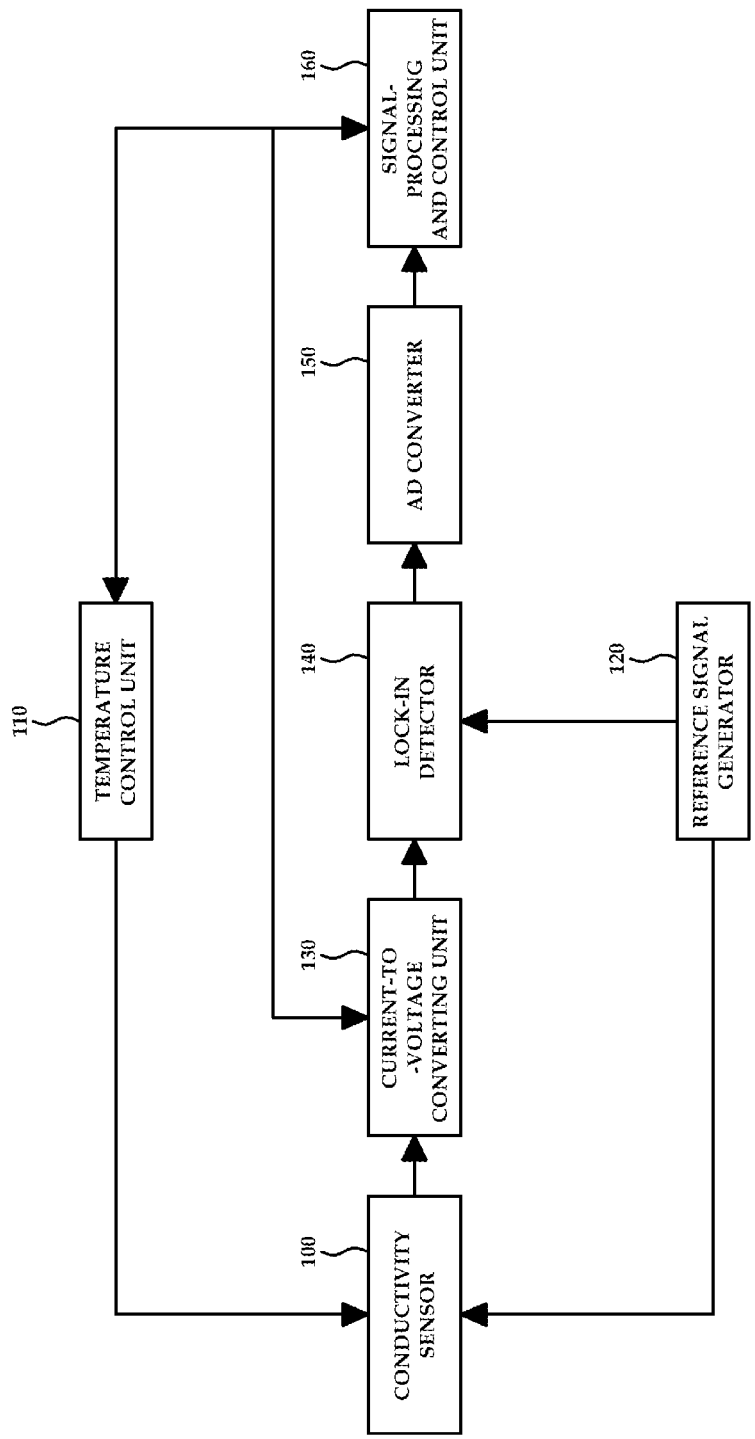
FIG. 2 is a block configuration diagram illustrating an apparatus for measuring electrical conductivity of liquid according to the preferred embodiment of the present invention.

FIG. 2 is a block diagram illustrating an apparatus for measuring electrical conductivity of liquid according to the preferred embodiment of the present invention.

As illustrated, the apparatus for measuring electrical conductivity of liquid according to the present invention includes a conductivity sensor 100 configured to detect conductivity of liquid and convert the conductivity into a current while maintaining its temperature at a desired constant level; a temperature control unit 110 configured to make the conductivity sensor 100 maintained at a constant temperature; a reference signal generator 120 configured to generate a reference signal and apply the reference signal to the conductivity sensor 100; a current-to-voltage converting unit 130 configured to convert the current output from the conductivity sensor 100 into a voltage; a lock-in detector 140 configured to synchronously demodulate and filter the voltage signal from the current-to-voltage converting unit 130, and amplify the voltage signal to a desired level; an AD converter 150 configured to convert an analog signal output from the lock-in detector 140 into a digital signal; and a signal-processing and control unit 160 configured to receive signals from the AD converter 150 and the temperature control unit 110, display conductivity measurement conditions and measurement states on a display unit 163 according to setting by a measurement-condition setting unit 164, transmit measured signals to an external apparatus, process various signals, and generate control commands for desired operations.

Modes for Carrying out the Invention

Figure 3:
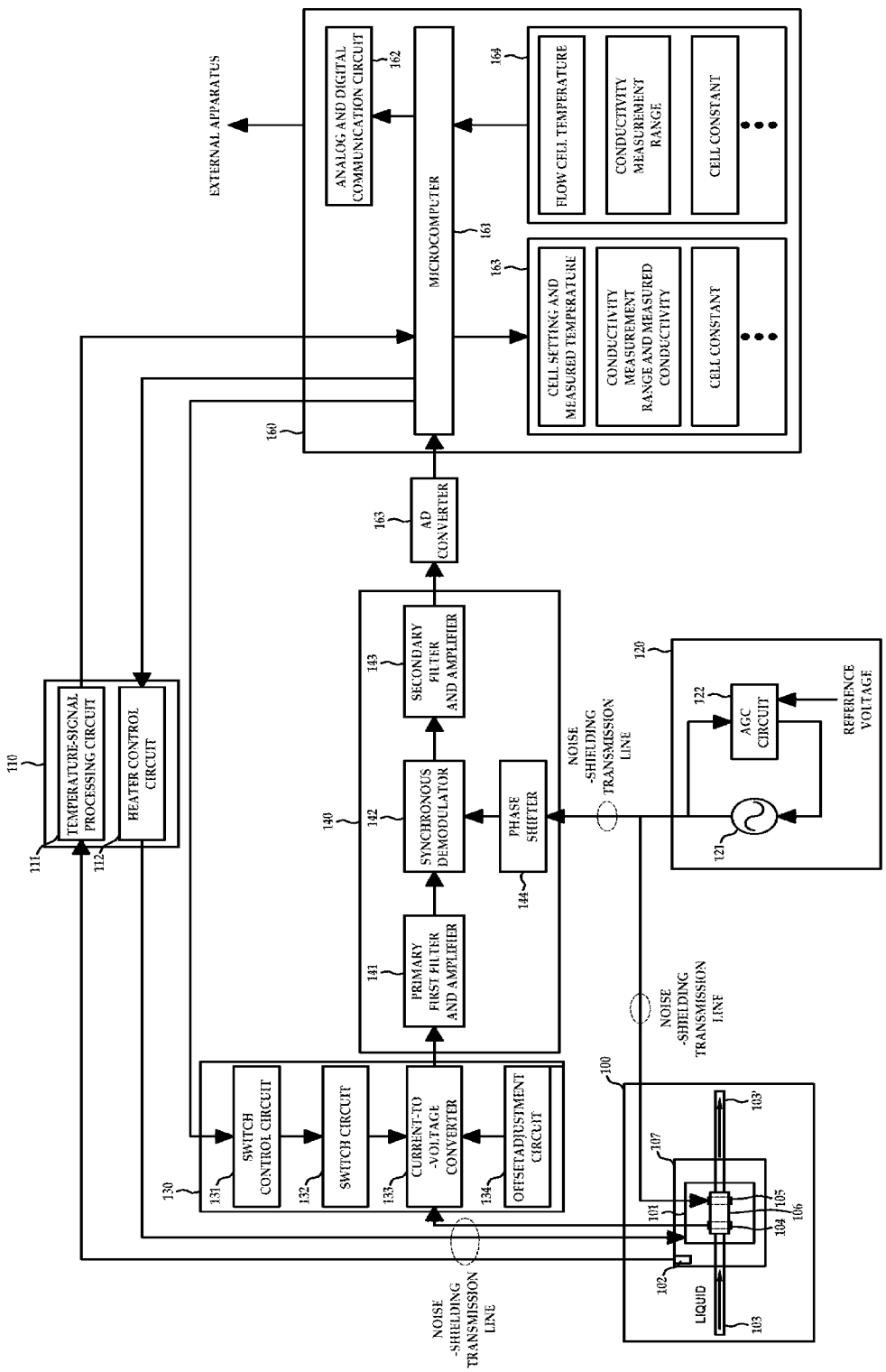
FIG. 3 is a detailed block configuration diagram illustrating an apparatus for measuring electrical conductivity of liquid according to the present invention of FIG. 2.

FIG. 3 is a detailed block configuration diagram illustrating an apparatus for measuring electrical conductivity of liquid according to the present invention of FIG. 2.

The conductivity sensor 100 includes inlet and outlet tubes 103 and 103' formed of fluororesin (for example, a Teflon tube may be used) and configured to guide the liquid; a flow cell 106 connected between the inlet and outlet tubes 103 and 103', and configured to receive the reference signal and convert the reference signal into a current proportional to the conductivity of the liquid; a mechanism 107 configured to fix the flow cell 106; a heater 101 configured to surround the cell fixing mechanism 107 and heat the liquid flowing in the flow cell 106 therethrough; a temperature sensor 102 inserted in the cell fixing mechanism 107 and configured to detect a temperature of the liquid in the flow cell 106; a reference-signal supply terminal 105 and a conductivity detection terminal 104 configured respectively to apply the reference signal to the liquid in the flow cell 106 and output a current proportional to the conductivity of the liquid, and supported by the cell fixing mechanism 107. Here, change in the conductivity of the liquid passing through the flow cell 106 becomes a conductivity signal, and the current output from the conductivity detection terminal 104 becomes a reference signal modulated by the conductivity signal. The reference-signal supply terminal 105 that supplies the reference signal to the flow cell 106 and the conductivity detection terminal 104 that outputs the current propotional to the conductivity of the liquid in the cell may be installed respectively in one side or several positions of the flow cell 106. Each terminal may be configured of two or more electrodes to detect conductivity accurately. The reference-signal supply terminal 105 may be connected to the reference signal generator 120 using a transmission line having a noise-shielding function such as a coaxial cable or a shielded twisted pair (STP) cable to guarantee the accuracy and repeatability of conductivity measurements.

As illustrated, the conductivity sensor 100 according to the preferred embodiment of the present invention functions to guide liquid to be measured through the inlet and outlet tubes 103 and 103' formed of fluororesin into the flow cell 106, convert the reference signal to a current proportional to the conductivity of the liquid, and send the current to the current-to-voltage converting unit 130. The heater 101 and the temperature sensor 102 in the conductivity sensor 100 are used to keep a liquid temperature in the flow cell 106 at a desired constant level, and function to minimize fluctuations of a baseline of the conductivity detector and the liquid conductivity due to temperature variations. For example, as the temperature sensor 102, a temperature sensor such as pt-100 is inserted into the cell fixing mechanism 107 to be used so that the temperature of the liquid flowing in the flow cell may be accurately measured. Further, the heater 101 is installed to heat the cell 106 via the cell fixing mechanism 107, and thus control the temperature of the liquid in the cell 106 to be uniform and stable. Therefore, the cell fixing mechanism 107 may use a material having good thermal conductivity. Since the output signal from the conductivity sensor 100 is very weak when the conductivity is infinitesimal, the conductivity detection terminal 104 may be connected to the current-to-voltage converting unit 130 using a transmission line having a noise-shielding function such as coaxial cable or a STP cable.

To keep the temperature of the conductivity sensor 100 at a desired constant level, the temperature control unit 110 includes a temperature-signal processing circuit 111 configured to process a signal from the temperature sensor 102 and transmit the processed signal to the signal-processing and control unit 160, and a heater control circuit 112 configured to receive temperature control commands from the signal-processing and control unit 160 and control the heater 101. Since the conductivity of the liquid is changed depending on the temperature variation, the baseline and the measured conductivity may be maintained stable and accurate when the conductivity sensor 100 is maintained at a constant temperature. Thereby, the infinitesimal conductivity of the liquid may be measured with minimum error. In the present invention, the temperature of the conductivity sensor 100 may be controlled using an analog or digital methods based on an appropriate control algorithm.

As illustrated, temperature-signal processing circuit 111 according to the preferred embodiment of the present invention appropriately processes the output signal from the temperature sensor 102 and transmits the processed signal to the signal-processing and control unit 160. Further, the heater control circuit 112 functions to keep the temperature of the flow cell 106 at a desired constant level by receiving the temperature control commands from the signal-processing and control unit 160 and controlling the heater 102 in the conductivity sensor 100. Here, the temperature control commands are generated by comparing a setting temperature of the cell 106 set by the measurement-condition setting unit 164 with the temperature value input from the temperature-signal processing circuit 111. To minimize noise effects, the temperature control unit 110 may be connected to the temperature sensor 102 and the heater 101 in the conductivity sensor 100 using a transmission line having a noise-shielding function such as coaxial cable or a STP cable.

The reference signal generator 120 includes an oscillator 121 configured to generate an alternating current (AC) signal with a specific amplitude and frequency and supply the AC signal to the conductivity sensor 100, and an AGC circuit 122 configured to accurately measure the infinitesimal conductivity by controlling an amplitude of the reference signal generated from the oscillator 121 to be constant. The reference signal generator 120 functions to apply the stable reference signal to the conductivity sensor 100 and minimize the change in a baseline and measurement errors of the conductivity due to amplitude variations of the reference signal. Here, the amplitude and frequency of the reference signal may be suitably selected by considering the conductivity levels of the liquid and variation rate of the conductivity (frequency of the conductivity signal).

In the reference signal generator 120, the oscillator 121 functions to generate the reference signal with a stable frequency, and the AGC circuit 122 functions to control the amplitude of the reference signal to be constant. Here, it 120 may be configured so that the amplitude level of the reference signal may be set by a reference voltage applied to the AGC circuit 122. In the conductivity measurements, since the output signal of the conductivity sensor 100 is generated in proportional to the amplitude of the reference signal as well as the liquid conductivity, the fluctuation in the amplitude of the reference signal is directly related to the measurement errors. Therefore, the AGC function of the reference signal generator 120 is a function necessarily required to measure the infinitesimal conductivity. However, the reference signal generator may be configured without the AGC function, depending on required lower limit and accuracy of the measurements.

As illustrated, the reference signal generator 120 according to a preferred embodiment of the present invention generates a reference signal, and applies the reference signal to the reference-signal supply terminal 105 in the conductivity sensor 100 so that the flow cell 106 may convert the reference signal into a current proportional to the conductivity of the liquid. The apparatus may generate AC signals having various waveforms, and include an AGC function and a function to adjust the amplitude of the reference signal so as to guarantee repeatability of measurements, measurement accuracy, and amplitude stability of the reference signal over time. To minimize noise and interference effects, the output of the reference signal generator 120 may be connected to the conductivity sensor 100 using a transmission line having a noise-shielding function such as coaxial cable or a STP cable.

The current-to-voltage converting unit 130 includes a current-to-voltage converter 133 configured to convert the output current from the conductivity sensor 100 into a voltage, an offset adjustment circuit 134 configured to adjust an output offset value of the current-to-voltage convertor 133, a switch circuit 132 configured to set a measurement range of the conductivity detector, and a switch control circuit 131 configured to control the switch circuit 132.

The current-to-voltage converting unit 130 converts the output current from the conductivity sensor 100 into a voltage and is configured of low-noise devices to enhance sensitivity of the conductivity measurements. Further, the current-to-voltage converting unit 130 may change a measurement range of the conductivity detector by changing a gain of the current-to-voltage converter 133, and adjusting an output offset of the converter 133. The switch circuit 132 may be controlled using the switch control circuit 131.

As illustrated, the current-to-voltage converting unit 130 according to a preferred embodiment of the present invention may allow the lock-in detector 140 to process the signal in a voltage type by converting the current signal from the conductivity sensor 100 into a low-noise voltage. Further, to change a conductivity measurement range, the current-to-voltage converting unit 130 may include the switch circuit 132 configured to change the gain of the current-to-voltage converter 133 and the offset adjustment circuit 134 configured to adjust the output offset of the current-to-voltage converter 133. In case the conductivity measurement range is fixed to a certain value, the switch circuit 132 and the switch control circuit 131 may be omitted. When the output offset of the current-to-voltage converter is acceptable in the measurements, the offset adjustment circuit 134 may also be omitted.

The lock-in detector includes a primary filter and amplifier 141 configured to filter and amplify the voltage output from the current-to-voltage converting unit 130, a synchronous demodulator 142 configured to synchronously demodulate the signal from the primary filter and amplifier 141, a secondary filter and amplifier 143 configured to filter and amplify the signal output from the synchronous demodulator 142, and a phase shifter 144 configured to synchronize a phase of the reference signal with a phase of the input signal of the synchronous demodulator 142. The synchronous demodulator 142 and the primary and secondary filter and amplifiers 141 and 143 reduces noise bandwidth to improve a signal-to-noise ratio (SNR) of the conductivity detector, and thus the lock-in detector 140 using the synchronous demodulator and filter and amplifiers becomes very suitable for measurements of infinitesimal conductivity.

As illustrated, the lock-in detector according to the preferred embodiment of the present invention is configured of the synchronous demodulator 142, the primary and secondary filter and amplifiers 141 and 143, and the phase shifter 144, and has a function to effectively detect a conductivity signal much smaller than noises and interference signals at a frequency of the reference signal. The primary filter and amplifier 141 filters and amplifies the output signal from the current-to-voltage converting unit 130 with a frequency bandwidth which may accommodate the modulated reference signal (a current proportional to the conductivity of the liquid), and functions to remove noises and interference signals present outside its passband. Further, the synchronous demodulator 142 functions to synchronously demodulate the output signal from the primary filter and amplifier 141 at a frequency of the reference signal included therein, and accurately detect even the very weak conductivity signal by removing the noises and interferences uncorrelated with the conductivity signal in its passband. The secondary filter and amplifier 143 functions to filter and amplify the output signal from the synchronous demodulator 142 with a frequency bandwidth that may suitably accommodate the conductivity signal, and remove the noises and interferences present outside its passband to improve an SNR of the conductivity detector. The primary and secondary filter and amplifiers 141 and 143 may have an appropriate gain to maintain an output signal level of the lock-in detector 140 within an input range of the AD converter 150. To perform effective detection in which output is maximized, the lock-in detector 140 may include the phase shifter 144 configured to adjust a phase of the reference signal applied thereto. When a phase difference between the reference signal included in the input signal of the synchronous demodulator 142 and the reference signal from the reference signal generator 120 is acceptable for the detection of a conductivity signal, the phase shifter 140 may be omitted. Further, when it is unnecessary to remove noises and interference signals contained in the output signal from the current-to-voltage converting unit 130, the primary filter and amplifier 141 may be omitted. To minimize noises and interferences, the phase shifter 144 may be connected to the reference signal generator 120 using a transmission line having a noise-shielding function such as coaxial cable or a STP cable.

The AD converter 150 is an apparatus configured to convert a conventional analog signal into a digital signal to process a signal in a digital signal type. However, when the user requires an analog signal, the AD converter may be omitted.

The signal-processing and control unit 160 includes a measurement-condition setting unit 164, measurement-condition and measurement-state display unit 163, an analog and digital communication circuit 162, and a microcomputer 161. The measurement-condition setting unit 164 is configured to set a conductivity measurement range of the conductivity measurement apparatus, an operation temperature of the flow cell, a cell constant, and the like. The measurement-condition and measurement-state display unit 163 is configured to display the items set by the measurement-condition setting unit 164, measured conductivity, a measured cell temperature, and the like on a display device such as a liquid crystal display (LCD). The analog and digital communication circuit 162 is configured to transmit conductivity signal received from the AD converter 150 or a temperature signal received from the temperature control unit 110 to an external apparatus. The microcomputer 161 is configured to process the measured conductivity and temperature signals and generate various control commands.

In the signal-processing and control unit 160, the measurement-condition setting unit 164 may be configured of selection buttons, up/down buttons, an enter button, and the like. The selection buttons are configured to select a conductivity measurement range, an operation temperature of the flow cell 106, a cell constant, and the like. The up/down buttons are configured to adjust a value of an item selected in the selection buttons, and the enter button is configured to set a value given by up/down button as a final value. The measurement-condition setting unit 164 transmits the conductivity measurement range, the cell setting temperature, the cell constant, and the like set from the setting buttons to the microcomputer 161.

In the signal-processing and control unit 160, the microcomputer 161 compares the cell setting temperature input from the measurement-condition setting unit 164 with the measured cell temperature received from the temperature control unit 110, transmits heater control commands to the heater control circuit 112, and controls the liquid temperature flowing in the flow cell 106 to a set temperature. The temperature of the flow cell 106 is set to be higher than maximum room temperature of an environment where the conductivity measurement apparatus is used. The temperature of the conductivity sensor 100 may be controlled in analog or digital methods using a suitable control algorithm.

Further, to set the conductivity measurement range, the microcomputer 161 transmits the range value received from the measurement-condition setting unit 164 to the switch control circuit 131 in the current-to-voltage converting unit 130, and the switch control circuit 131 controls the switch circuit. Thereby, the conductivity measurement range of the conductivity detector is set to a range value by the setting buttons. The conductivity measurement range of the current-to-voltage converting unit 130 may be controlled in analog or digital methods using a suitable control algorithm. In addition, the microcomputer 161 may perform signal processing for the measurement-condition and measurement-state display unit 163, the analog/digital communication circuit 162, and the like.

In the signal-processing and control unit 160, the measurement-condition and measurement-state display unit 163 displays items (conductivity measurement range, cell setting temperature, cell constant, and the like) set by the measurement-condition setting unit 164, measured conductivity, and measured cell temperature, and the like on a display device such as an LCD to allow the user to conveniently recognize the conductivity measurement conditions and measurement states.

In the signal-processing and control unit 160, the analog and digital communication circuit 162 is an apparatus configured to transmit measured conductivity or a measured temperature of the flow cell 106 to an external apparatus, using analog or digital methods.

The foregoing is illustrative of embodiments and is not to be construed as limiting thereof. Although a few embodiments have been described, those skilled in the art will readily appreciate that many modifications are possible in embodiments without materially departing from the novel teachings and advantages. Accordingly, all such modifications are intended to be included within the scope of this inventive concept as defined in the claims. In the claims, means-plus-function clauses are intended to cover the structures described herein as performing the recited function, and not only structural equivalents but also equivalent structures.

INDUSTRIAL APPLICABILITY

According to the an apparatus for measuring electrical conductivity of liquid, infinitesimal conductivity of liquid can be consistently and accurately measured, and change in the performance of the detection apparatus over time can be minimized, by minimizing temperature variations, unstability of a reference signal, and noise effects to ensure the stability of baseline as a measurement reference of the conductivity and accuracy of conductivity measurements.

The invention claimed is:

1. An apparatus for measuring electrical conductivity of liquid, the apparatus comprising:
  a conductivity sensor configured to detect conductivity of liquid and convert the detected conductivity into a current;
  a temperature control unit configured to collect a temperature of the conductivity sensor and control its temperature to a desired constant level;
  a reference signal generator configured to generate a reference signal and supply the reference signal to the conductivity sensor;
  a current-to-voltage converting unit configured to convert the current output from the conductivity sensor into a low-noise voltage;
  a lock-in detector configured to synchronously demodulate and filter an output voltage signal from the current-to-voltage converting unit, and amplify the signal to a desired level; and
  a signal-processing and control unit configured to not only receive the temperature collected in temperature control unit and generate control commands to constantly maintain the temperature of the conductivity sensor at a level set to be higher than room temperature of a measurement environment by setting of measurement conditions, but also calculate the liquid conductivity using a voltage signal from the lock-in detector, provide signal processing, and generate various control commands according to the setting of measurement conditions,
  wherein the conductivity sensor includes an inlet tube and an outlet tube configured to guide the liquid; and a flow cell with a constant cross section and a fixed length that is connected to the inlet tube at a cross section and the outlet tube at the other cross section, also includes a reference-signal supply terminal formed in one side thereof to supply a reference signal to the flow cell, and a conductivity detection terminal formed in the other side thereof to detect a current signal generated in proportional to the conductivity of the liquid flowing therein.

2. The apparatus according to claim 1, wherein the conductivity sensor includes a heater configured to heat the liquid in the flow cell.

3. The apparatus according to claim 2, wherein the temperature control unit includes a heater control circuit configured to receive the temperature control commands from the signal-processing and control unit to control the heater.

4. The apparatus according to claim 1, wherein the conductivity sensor includes a temperature sensor configured to detect a temperature of the liquid.

5. The apparatus according to claim 4, wherein the temperature control unit includes a temperature-signal processing circuit configured to process an output signal from the temperature sensor and transmit the processed signal to the signal-processing and control unit so as to keep the temperature of the flow cell at a desired constant level.

6. The apparatus according to claim 1, wherein the reference-signal supply terminal is formed in a plural number in at least two locations of the flow cell.

7. The apparatus according to claim 1, wherein the conductivity detection terminal is formed in a plural number in at least two locations of the flow cell.

8. The apparatus according to claim 1, wherein the inlet tube and the outlet tube are formed of fluororesin.

9. The apparatus according to claim 1, wherein the reference signal generator includes an oscillator configured to generate the stable reference signal with a specific amplitude and frequency.

10. The apparatus according to claim 9, wherein the reference signal generator includes an automatic gain control (AGC) circuit configured to control the amplitude of the reference signal generated from the oscillator to be constant.

11. The apparatus according to claim 1, wherein current-to-voltage converting unit includes a current-to-voltage converter configured to convert the current output from the conductivity sensor into the low-noise voltage.

12. The apparatus according to claim 11, wherein the current-to-voltage converting unit includes an offset adjustment circuit configured to adjust an output offset value of the current-to-voltage converter.

13. The apparatus according to claim 11, wherein the current-to-voltage converting unit includes a switch circuit configured to set a measurement range of the conductivity detector.

14. The apparatus according to claim 13, wherein the current-to-voltage converting unit includes a switch control circuit configured to control a switch circuit.

15. The apparatus according to claim 1, wherein the signal-processing and control unit includes a microcomputer configured to perform processing for the conductivity and temperature signals, and generate the temperature control commands.

16. The apparatus according to claim 15, wherein the signal-processing and control unit includes an analog and digital communication circuit configured to transmit a conductivity signal received from the lock-in detector or a temperature of a flow cell received from the temperature control unit to an external apparatus.

17. The apparatus according to claim 16, wherein the signal-processing and control unit includes a measurement-condition setting unit configured to set a conductivity measurement conditions of the apparatus for measuring electrical conductivity of liquid.

18. The apparatus according to claim 16, wherein the signal-processing and control unit includes a measurement-condition and measurement-state display unit configured to display the conductivity measurement conditions set by the measurement-condition setting unit and measurement states on a display device.

19. The apparatus according to claim 16, wherein the microcomputer generates control commands to the switch control circuit so as to adjust the conductivity measurement range.

20. The apparatus according to claim 1, further comprising one or more noise-shielding transmission lines configured to connect any one component among the reference signal generator, the current-to-voltage converting unit, and the temperature control unit to the conductivity sensor, or connect the lock-in detector to the reference signal generator.

21. The apparatus according to claim 1, wherein the lock-in detector includes a synchronous demodulator configured to synchronously detect the signal output from the current-to-voltage converting unit.

22. The apparatus according to claim 21, wherein the lock-in detector includes a secondary filter and amplifier configured to filter and amplify a signal output from the synchronous demodulator.

23. The apparatus according to claim 21 wherein the lock-in detector includes a primary filter and amplifier configured to filter and amplify an output signal of the current-to-voltage converting unit and to transmit the filtered and amplified signal to the synchronous demodulator.

24. The apparatus according to claim 21, wherein the lock-in detector includes a phase shifter configured to adjust a phase of the reference signal and synchronize the reference signal with an input signal of the synchronous demodulator.

25. An apparatus for measuring electrical conductivity of liquid, the apparatus comprising:
   a conductivity sensor configured to detect conductivity of liquid and convert the detected conductivity into a current;
   a temperature control unit configured to collect a temperature of the conductivity sensor and control its temperature to a desired constant level;
   a reference signal generator configured to generate a reference signal and supply the reference signal to the conductivity sensor;
   a current-to-voltage converting unit configured to convert the current output from the conductivity sensor into a low-noise voltage;
   a lock-in detector configured to synchronously demodulate and filter an output voltage signal from the current-to-voltage converting unit, and amplify the signal to a desired level; and
   a signal-processing and control unit configured to not only receive the temperature collected in temperature control unit and generate control commands to constantly maintain the temperature of the conductivity sensor at a level set to be higher than room temperature of a measurement environment by setting of measurement conditions, but also calculate the liquid conductivity using a voltage signal from the lock-in detector, provide signal processing, and generate various control commands according to the setting of measurement conditions, wherein the lock-in detector includes a synchronous demodulator configured to synchronously detect the signal output from the current-to-voltage converting unit.

26. The apparatus according to claim 25, wherein the lock-in detector includes a secondary filter and amplifier configured to filter and amplify a signal output from the synchronous demodulator.

27. The apparatus according to claim 25 wherein the lock-in detector includes a primary filter and amplifier configured to filter and amplify an output signal of the current-to-voltage converting unit and to transmit the filtered and amplified signal to the synchronous demodulator.

28. The apparatus according to claim 25, wherein the lock-in detector includes a phase shifter configured to adjust a phase of the reference signal and synchronize the reference signal with an input signal of the synchronous demodulator.

29. An apparatus for measuring electrical conductivity of liquid, the apparatus comprising:
   a conductivity sensor configured to detect conductivity of liquid and convert the detected conductivity into a current;
   a temperature control unit configured to collect a temperature of the conductivity sensor and control its temperature to a desired constant level;
   a reference signal generator configured to generate a reference signal and supply the reference signal to the conductivity sensor;
   a current-to-voltage converting unit configured to convert the current output from the conductivity sensor into a low-noise voltage;
   a lock-in detector configured to synchronously demodulate and filter an output voltage signal from the current-to-voltage converting unit, and amplify the signal to a desired level; and
   a signal-processing and control unit configured to not only receive the temperature collected in temperature control unit and generate control commands to constantly maintain the temperature of the conductivity sensor at a level set to be higher than room temperature of a measurement environment by setting of measurement conditions, but also calculate the liquid conductivity using a voltage signal from the lock-in detector, provide signal processing, and generate various control commands according to the setting of measurement conditions,
   the signal-processing and control unit includes a microcomputer configured to perform processing for the conductivity and temperature signals, and generate the temperature control commands,
   wherein the signal-processing and control unit includes an analog and digital communication circuit configured to transmit a conductivity signal received from the lock-in detector or a temperature of a flow cell received from the temperature control unit to an external apparatus.

30. The apparatus according to claim 29, wherein the signal-processing and control unit includes a measurement-condition setting unit configured to set a conductivity measurement conditions of the apparatus for measuring electrical conductivity of liquid.

31. The apparatus according to claim 29, wherein the signal-processing and control unit includes a measurement-condition and measurement-state display unit configured to display the conductivity measurement conditions set by the measurement-condition setting unit and measurement states on a display device.

32. The apparatus according to claim 29, wherein the microcomputer generates control commands to the switch control circuit so as to adjust the conductivity measurement range.

* * * * *